United States Patent [19]

Sanzo et al.

[11] Patent Number: 4,957,863
[45] Date of Patent: Sep. 18, 1990

[54] METHOD OF INCREASING YIELD OF T-PA IN CELL CULTURE

[75] Inventors: Michael A. Sanzo, St. Louis; Medora M. Hardy, Chesterfield; Joseph Feder, St. Louis, all of Mo.

[73] Assignee: Monsanto Company, St. Louis, Mo.

[21] Appl. No.: 148,409

[22] Filed: Jan. 26, 1988

[51] Int. Cl.$^5$ ............................................. C12N 9/64
[52] U.S. Cl. ............................ 435/228; 435/212; 435/219; 435/240.23
[58] Field of Search .................... 435/212, 226, 240.23

[56] References Cited

U.S. PATENT DOCUMENTS

| | | | |
|---|---|---|---|
| 4,335,215 | 6/1982 | Tolbert et al. | 435/241 |
| 4,537,860 | 8/1985 | Tolbert et al. | 435/240 |
| 4,833,085 | 5/1989 | Schaumann et al. | 435/240.27 |

FOREIGN PATENT DOCUMENTS 219270  4/1987  European Pat. Off. .

OTHER PUBLICATIONS

Einarsson, M., et al. (1985), Biochim. Biophys. Acta 830, 1–10.
Reagan, M. E., et al. (1985), Thromb. Res. 40, 1–9.
Kadouri and Bohak, Adv. Biotech, Proc. 5, Ed. Mizrahi and van Wezel, Alan R. Liss, Inc. 1985, pp. 275–299.
Jones and Griffen, Chem. Week, Apr. 1, 1987, pp. 38–41.
Arathoon and Birch, Science 232, 1390–1395 (1986).
Adamson and Schmidli, Can. J. Chem. Eng. 64, 531–539 (1986).

*Primary Examiner*—Elizabeth C. Weimar
*Assistant Examiner*—Charles L. Patterson
*Attorney, Agent, or Firm*—Scott J. Meyer; James W. Williams, Jr.

[57] ABSTRACT

A method is disclosed for increasing the yield of t-PA in culture of mammalian cells comprising introducing antibodies to the t-PA of said cells into the cell culture nutrient medium, allowing the cells to grow, and then recovering t-PA from the t-PA-antibody complex thus found in the conditioned medium by exchanging antibody in the complex for t-PA antibody immobilized on an inert support.

7 Claims, 2 Drawing Sheets

METHOD OF INCREASING YIELD OF T-PA IN CELL CULTURE

BACKGROUND OF THE INVENTION

This invention relates to the cell culture production of the thrombolytic agent tissue plasminogen activator. More particularly, the invention relates to a method for increasing the yield of tissue plasminogen activator in culture of mammalian cells.

It is known that various plasminogen activators (PA) are widely distributed throughout the body and can be purified from tissue extracts. Typical examples of tissue sources are kidney, lung and uterus tissues. The best characterized of these plasminogen activators fall into two major groups, urokinase plasminogen activator (u-PA) and tissue plasminogen activator (t-PA). u-PA and t-PA are present in ng/ml concentrations in human plasma and are immunologically unrelated. t-PA has been demonstrated to have higher affinity for fibrin than u-PA. u-PA products isolated and purified from human urine and from mammalian kidney cells are pharmaceutically available as thrombolytic agents.

Due to the extremely low concentration of t-PA in blood and tissue extracts, other sources and means of producing this preferred thrombolytic agent have been sought after.

One method of producing t-PA on a large scale comprises isolating the protein from the culture fluid of human melanoma cells grown under in vitro cell culture conditions. An established human melanoma cell line (Bowes) has been used for this purpose. See, for example, European Patent Application No. 41,766, published Dec. 16, 1981; Rijken and Collen, *J. Biol. Chem.* 256(13), 7035–7041 (1981); and Kluft et al., *Adv. Biotech. Proc.* 2, Alan R. Liss, Inc., 1983, pp. 97–110. The Bowes melanoma t-PA is a glycoprotein which has a molecular weight of about 68,000–70,000 daltons and a 527 amino acid structure with serine at the $NH_2$-terminus. The melanoma t-PA can exist as two chains, an A-chain and a B-chain. It also separates into two variants (or isoforms) in the A-chain, known as types I and II which differ by about $M_r$ 2000-3000. See Ranby et al., *FEBS Lett.* 146 (2), 289–292 (1982), and Wallen et al., *Eur. J. Biochem.* 132, 681–686 (1983). Type I is glycosylated at Asn-117, Asn-184 and Asn-448 whereas Type II is glycosylated only at Asn-117 and Asn-448 according to Pohl et al., *Biochemistry* 23, 3701–3707 (1984). A high mannose structure has been assigned to Asn-117 whereas two complex carbohydrate structures are assigned to Asn-184 and Asn-448 by Pohl et al., "EMBO Workshop on Plasminogen Activators," Amalfi, Italy, Oct. 14–18, 1985.

Genetic information from the Bowes melanoma cell line also has been embodied in *E. coli* by conventional recombinant DNA gene splicing methods to permit the production of the t-PA protein moiety by that microorganism. See, for example, UK Patent Application No. 2,119,804, published Nov. 23, 1983; Pennica et al., *Nature* 301, 214–221 (1983); and Vehar et al., *Bio/Technology* 2 (12), 1051–1057 (1984). Recombinant t-PA produced by the expression of Bowes melanoma genetic material in cultured mammalian cells has been administered to humans with some measure of effectiveness. See Collen et al., *Circulation* 70(16), 1012–1017 (1984).

The recombinant-derived t-PA produced in *E. coli* is non-glycosylated and contains only the protein moiety of t-PA. Although the specific function of the carbohydrate moiety on t-PA has not been determined, it is known, in general, that glycosylation can cause certain differences of which the following are of biological interest: antigenicity, stability, solubility and tertiary structure. The carbohydrate side-chains also can affect the protein's half-life and target it to receptors on the appropriate cells. See, for example, Delente, *Trends in Biotech.* 3(9), 218 (1985), and Van Brunt, *Bio/Technology* 4, 835–839 (1986). The functional properties of carbohydrate-depleted t-PA are further discussed by Little, et al., *Biochemistry* 23, 6191–6195 (1984), and by Opdenakker et al., "EMBO workshop on Plasminogen Activators," Amalfi, Italy, Oct. 14–18, 1985. The latter scientists report that enzymatic cleavage of carbohydrate side-chains from the melanoma (Bowes) derived t-PA by treatment with α-mannosidase causes an increase in the biologic activity of the modified t-PA.

Cultured normal human cells also have been used as a source of t-PA as can be seen from U.S. Pat. Nos. 4,335,215, 4,505,893, 4,537,860, and 4,550,080. Various cell sources mentioned in said patents are primary embryonic (or fetal) kidney, lung, foreskin, skin and small intestines (Flow Laboratories) or the AG1523 cell line. Brouty-Boye et al., *Bio/Technology* 2 (12), 1058–1062 (1984), further disclose the use of normal human embryonic lung cells for the production of t-PA. Rijken and Collen, *J. Biol. Chem.* 256(13), 7035–7041 (1981), and Pohl et al., *FEBS Lett.* 168(1), 29–32 (1984), disclose the use of human uterine tissue as a t-PA source material. European Patent Application No. 236,289, published Sept. 9, 1987, describes a uniquely glycosylated t-PA derived from normal human colon fibroblast cells.

Production of glycosylated t-PA in non-human mammalian cells also is known. Thus, Kaufman et al., *Mol. Cell. Biol.* 5, 1750–1759 (1985), and European Patent Application No. 117,059, published Aug. 29, 1984, describe the use of Chinese hamster ovary cells and Browne et al., *Gene* 33, 279–284 (1985), describe the use of mouse L cells for such production. Kaufman et al., state that the Chinese hamster ovary t-PA is glycosylated in a similar but not identical manner as native t-PA. Glycosylated forms of t-PA obtained by recombinant DNA are further described by Zamarron et al., *J. Biol. Chem.* 259 (4), 2080–2083 (1984), and Collen et al., *J. Pharmacol. Expertl. Therap.* 231 (1), 146–152 (1984).

Notwithstanding the advantages in the production of t-PA by culture of mammalian cells, it has been found that such production is regulated by negative feedback which in turn is controlled by the concentration of the extracellular t-PA. Various methods have been reported heretofore to minimize the effects of the negative feedback on the biosynthesis of t-PA. One method is to use a high ratio of medium volume to cell number so that the extracellular t-PA does not reach a high concentration. Another method is to perfuse the system continuously, thereby removing part of the t-PA containing medium and replacing it with fresh medium. Still another method is to adsorb the product continuously and to recycle the supernatant. See Kadouri and Bohak in *Adv. Biotechnological Proc.* 5, Eds. Mizrahi and van Wesel, Alan R. Liss, Inc., 1985, pp. 275–299.

BRIEF DESCRIPTION OF THE INVENTION

In accordance with the present invention a novel method is provided for increasing the yield of tissue plasminogen activator (t-PA) in culture of mammalian cells. The method comprises introducing antibodies to the t-PA of said cells into the cell culture nutrient medium, allowing the cells to grow and then recovering t-PA from the t-PA-antibody complex thus formed in the conditioned medium by exchanging antibody in the complex for t-PA antibody immobilized on an inert support.

In this method, it is important that the monoclonal antibody should be one which recognizes an epitope on the t-PA produced by the particular mammalian cells in culture. The t-PA then binds to the immobilized antibody during the exchange step at low ionic concentration and can be released by subsequent elution with a high concentration of KSCN. It is preferred that a salt (NaCl) concentration of about 0.15 molar or less be used for the t-PA binding and a KSCN concentration of about 2.0 molar or greater be used for the t-PA elution in the exchange step.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings in which:

Figure 1:
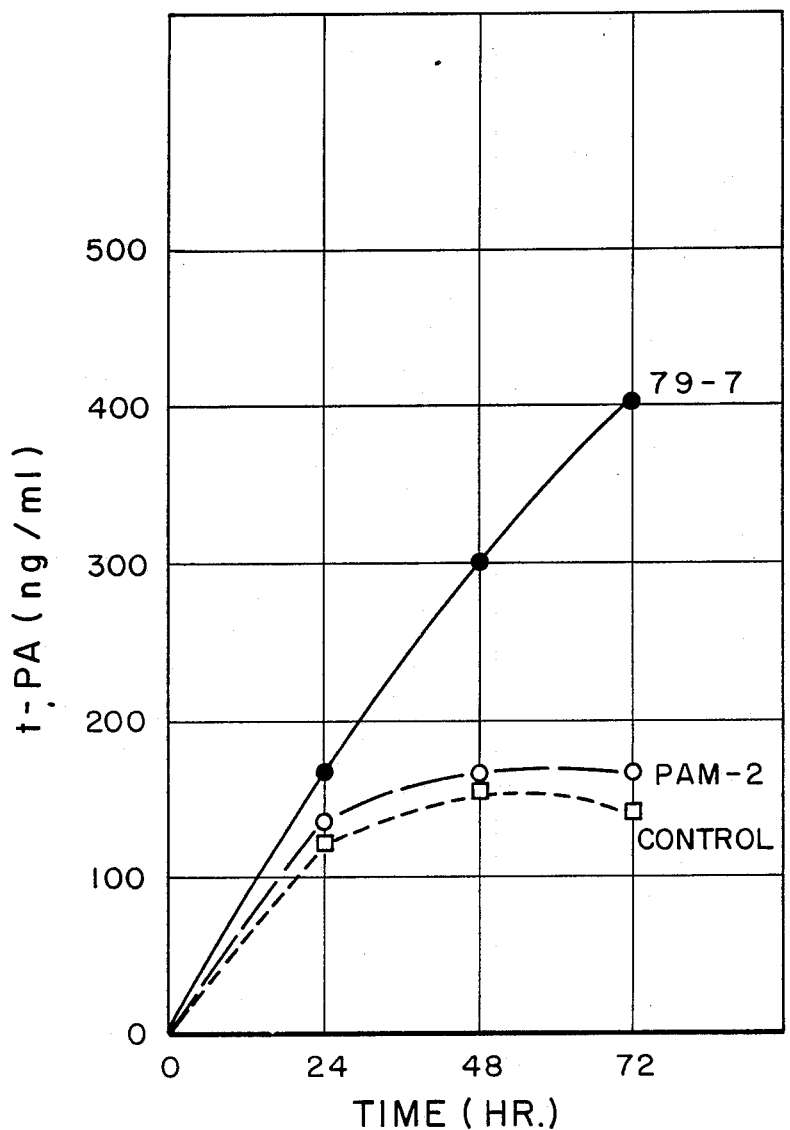
FIG. 1 is a graphical representation which shows the concentration of t-PA in ng/ml over time in hours in a preferred embodiment of the invention in which t-PA monoclonal antibody 79-7 is introduced into the cell culture nutrient medium of normal human colon fibroblast cells CCD-18Co and compared to similar runs with PAM-2 t-PA antibody or no antibody (control).

The invention is illustrated in greater detail herein by the production and recovery of t-PA in the cell culture of the human colon fibroblast cell line CCD-18Co. The uniquely glycosylated t-PA derived from these cells and its production in nutrient cell culture media are described in copending applications Ser. No. 849,933, filed Apr. 9, 1986, and Ser. No. 929,950, filed Nov. 12, 1986, now U.S. Pat. No. 4,751,084 and in European Patent Application No. 236,289, published Sept. 9, 1987, the disclosures of which are incorporated herein by reference.

The CCD-18Co cell line is on deposit without restriction in the permanent collection of the American Type Culture Collection, Rockville, Md., under accession number ATCC CRL-1459.

This cell line was originally cultured in CRCM medium with 20% fetal bovine serum and antibiotics. CRCM is a nutrient medium developed by the American Type Culture Collection. During passage, the medium was changed to minimum essential medium (Eagle) with non-essential amino acids in Earle's BSS (balanced salt solution) supplemented with 10% fetal bovine serum. These cells also can be cultured in other well-known cell culture media such as basal medium Eagle's (BME), Dulbecco's modified Eagle medium (DMEM), medium 199, RPMI 1640 medium, and the like cell culture media such as described in detail by H. J. Morton, In Vitro 6, 89–108 (1970). These conventional culture media contain known amino acids, mineral salts, vitamins, hormones and carbohydrates. They are also frequently fortified with mammalian sera such as fetal bovine serum Other components which are desirably used in the media are protein hydrolysates such as lactalbumin hydrolysate, tryptone, tryptose, peptone and the like materials.

Methods for the large scale growth of mammalian cells are well-known and these methods can be used for the culture of the colon cells defined herein. Such methods are described, for example, by Tolbert et al., Biotech. Bioeng. XXIV, 1671–1679 (1982); Tolbert and Feder, Ann. Rept. Ferm. Proc., Vol. 6, Ch. 3, pp. 35–74 (1983); Harakas, Ibid. Vol. 7, Ch. 7, pp. 159–211 (1984); and references cited in said publications. U.S. Pat. Nos. 4,166,768; 4,289,854; 4,335,215; and 4,537,860 disclose particularly useful methods and apparatus for the large scale growth and maintenance of cells for the production of plasminogen activators. The disclosures in said patents are incorporated herein by reference. The methods and apparatus disclosed therein can be used for the culture of the colon cells defined herein.

The cells are preferably cultured in nutrient medium at 37° C. in agitated microcarrier suspension culture as described in U.S. Pat. No. 4,335,215 and, after a suitable growth period, are maintained in the static maintenance reactor described in U.S. Pat. No. 4,537,860 in which the medium is supplemented with 0.5% lactalbumin hydrolysate.

Monoclonal antibodies to the t-PA derived from normal human colon fibroblast cells are described in copending application Ser. No. 896,362, filed Aug. 13, 1986, now U.S. Pat. No. 4,833,085 the disclosure of which is incorporated herein by reference. Three preferred hybrid cell lines for use in making these antibodies are designated as cell lines PA 63-4, PA 54-2 and PA 79-7. They are more conveniently designated herein solely by the stated numbers without the PA prefix. Isolates of these hybrid cell lines are on deposit in the permanent collection of the American Type Culture Collection, Rockville, Md., under accession numbers ATCC HB 9155, ATCC HB 9157 and ATCC HB 1956, respectively.

The monoclonal antibody production can be carried out by conventional procedure such as described, for example by Köhler and Milstein, Nature 256, 495–497 (1975); Eur. J. Immunol. 6, 511–519 (1976). According to this method, tissue-culture adapted mouse myeloma cells are fused to spleen cells from immunized mice to obtain the hybrid cells that produce large amounts of a single antibody molecule. In this procedure, t-PA antigen bound to the carrier protein, preferably bovine serum albumin, is used as the immunogen. The carrier protein, which can be natural protein molecules, synthetic peptides, or equivalent polymeric particles, is used to enhance immunogenicity of the t-PA antigen. The albumins (e.g., human, bovine, or rabbit), synthetic peptides (e.g., polylysine) and polymers (e.g., polyvinylpyrrolidone) are commonly used as carriers for antibody production. The bovine serum albumin-derivatized t-PA can be prepared by conventional general procedure as described for example, by Lieberman et al., Rec. Prog. Hor. Res. 15, 165 (1959).

A preferred mouse myeloma cell line for use in making these antibodies is the Sp2/0-Ag 14 cell line. This is a well-known cell line of BALB/c origin defined by Schulman, Wilde and Köhler, Nature 276, 269–270 (1978), the disclosure of which is incorporated herein by reference. These cells, which do not synthesize Ig chains can be obtained from the Basel Institute for Immunology and are available to the public from the American Type Culture Collection, Rockville, Md., under accession number ATCC CRL-1581. A preferred method of carrying out the fusion of the myeloma cells and the spleen cells is by the conventional general procedure described by Galfre et al., *Nature* 266, 550–552 (1977). This method employs polyethylene glycol (PEG) as the fusing agent for the cells growing as monolayers followed by selection in HAT medium (hypoxanthine, aminopterin and thymidine) as described by Littlefield, *Science* 145, 709–710 (1964).

It will be appreciated that not all hybridomas prepared as described herein will have optimum antibody activity. As is customary in this field, radioimmunoassay procedures can be readily used to screen the population of hydridomas for individual clones which secrete the optimum specificity. The radioimmunoassay is based upon the competition between radiolabeled and unlabeled antigen for a given amount of antibody which can be determined by conventional general procedure as described, for example, by Yalow et al., *J. Clin. Invest.* 39, 1157 (1960).

For recovery of the t-PA from the t-PA-antibody complex, the antibody in the complex is exchanged for antibody immobilized on an inert support. A material such as agarose or Sepharose ® (spherical agarose gel particles available from Pharmacia) is a preferred substance for the inert support. The t-PA antibody immobilized on the inert support can be incubated with the conditioned media in a batch process for carrying out the antibody exchange step, but passage of the conditioned media over the immobilized antibody in a conventional immunochromatographic column configuration is preferred. The latter process can be carried out on a continuous basis by recycling the unbound conditioned media which contains the released t-PA antibodies back to the cell culture vessel for complexing with additionally produced t-PA. (see FIG. 2).

The following examples will further illustrate the invention although it will be understood that the invention is not limited to these specific examples.

Example 1

Human colon fibroblasts (CCD-18Co) were grown in 25 cm$^2$ Nunc culture flasks using Dulbecco's Modified Eagle's Medium (DMEM) supplemented with 10% fetal bovine serum (FBS) until confluent monolayers were obtained. Monolayers were washed twice with 3.0 ml aliquots of phosphate buffered saline (PBS). 5.0 ml of fresh DMEM+10% FBS was applied and monolayers were incubated at 37° C. in an atmosphere of 6% CO$_2$. Aliquots for t-PA ELISA assays were taken at 24-hour intervals from the time when the fresh medium was applied to the cells (time zero). Cell density was estimated from cell counts taken at time zero, at 72 hours and 96 hours. The counts were made by trypsinizing cells off replica wells and taking readings using a Coulter Counter ®. All samples were done in triplicate. The results obtained are shown in Table 1, below. It was found that the cell density remained constant throughout the test. The t-PA concentration increased during the first 24 hours and decreased slowly thereafter.

Example 2

CCD-18Co cells were grown to confluency and incubated as described in Example 1. Flasks received either PAM 2 or 79-7 antibody to t-PA at doses of 1 μg/ml at time zero and at 24-hour intervals thereafter. Control flasks received no antibody. In each instance samples for ELISA assays were taken immediately before the next dose of antibody was administered. It is apparent from both FIG. 1 and Table 2, below, that the antibody 79-7 dramatically increases the concentration of t-PA in the CCD-18Co conditioned medium. In contrast to the t-PA concentrations in control samples which plateaued at 48 hours, the concentration in the samples from 79-7 supplemented flasks appears to still be increasing at 72 hours. PAM 2, another monoclonal antibody to t-PA, had no effect. It, therefore, appears that the particular epitope recognized by the antibody is of importance in determining whether or not it will promote t-PA accumulations in the conditioned medium.

Example 3

As described in Example 2, 79-7 monoclonal antibody can be used to increase the concentration of t-PA in CCD-18Co conditioned medium. However, to be of most practical value, the complexes thus generated must be in a form which will allow t-PA to be recovered from the medium. In order to provide this, the conditioned medium from Example 2 containing 79-7 t-PA complexes was incubated with 1.0 ml of PAM 2-Sepharose overnight at 4° C. and then for 4 hours at room temperature. It was found that approximately half (50.5%) of the t-PA antigen in the conditioned medium was not bound by the immobilized PAM 2. Since virtually all of the t-PA in the conditioned medium should have been in the form of the same t-PA-antibody complex, this result suggested that PAM 2 competed relatively poorly for the 79-7 binding site and that a different antibody might be more effective. In other tests, it had been found that PAM 2 immobilized onto Sepharose was capable of exchanging for the PAM 2 bound to t-PA in conditioned medium and, by analogy, it was thought that immobilized 79-7 might be an effective competitor for 79-7 complexes in conditioned medium. In order to test this, the 79-7 t-PA fraction, unadsorbed by PAM 2-Sepharose (50.5%, 13 ml), was divided in half. One-half (6.5 ml) was incubated with approximately 1.0 ml of PAM 2-Sepharose as before, and the other half (6.5 ml) was incubated with approximately 1.0 ml of 79-7-Sepharose. After incubating overnight at 4° C., and for 4 hours at room temperature, the Sepharoses were packed in columns and the effluent containing the unadsorbed proteins was collected. The columns were washed in buffer [0.02 M sodium phosphate (pH 6.8), 0.15 M NaCl, 0.05% Tween 20] containing 0.25 M KSCN and were then eluted in the same buffer containing a concentration of KSCN known to completely elute t-PA (2.0 M for PAM 2-Sepharose and 3.0 M for 79-7-Sepharose). The results of the final set of ELISA assays is shown in Table 3, below.

In the above processing of the conditioned media it was observed that when the fraction unadsorbed by the first PAM 2 column is reapplied to PAM 2 a second time, 67% of the t-PA remains unadsorbed. About 20% of the antigen applied to the column was found in the fraction eluted with 2.0 M KSCN. In contrast, essentially all (113%) of the t-PA applied to the 79-7-Sepharose column was bound and recovered. This result indicates that 79-7 can be used, not only for increasing t-PA concentrations in conditioned medium but also for recovering the t-PA from the same medium.

In the foregoing examples, t-PA ELISA assays were performed using reagents purchased from American Diagnostica Inc. and following their recommended procedures. PAM 2 antibody and PAM 2 immobilized on Sepharose were also purchased from American Diagnostica.

Figure 2:
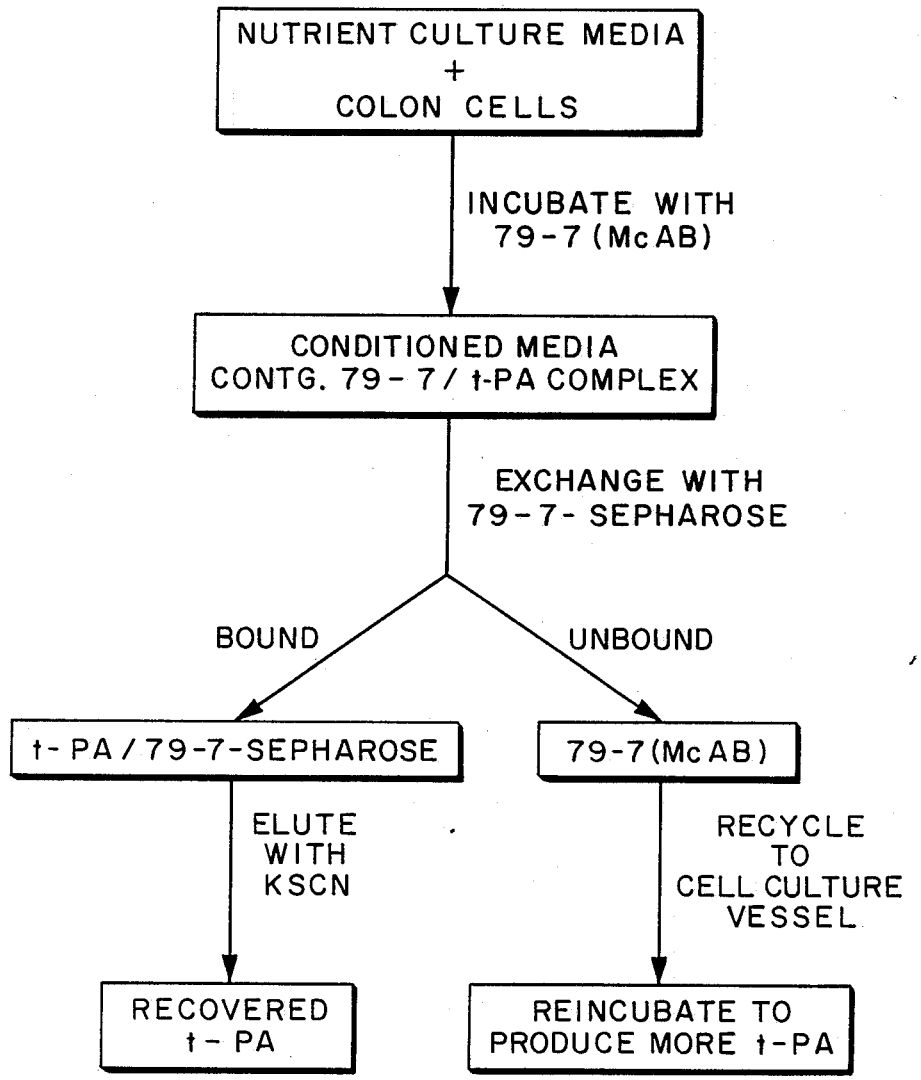
FIG. 2 is a schematic outline which shows the incubation of the colon cell culture medium of FIG. 1 with the 79-7 monoclonal antibody followed by the processing of the resulting t-PA-antibody complex from the conditioned media in another preferred embodiment of the invention.

FIG. 2 illustrates a preferred embodiment of the invention in which the antibody exchange step avoids the intermediate treatment with PAM 2-Sepharose but in which the conditioned media is directly incubated with the 79-7-Sepharose. In this case, the unbound 79-7 monoclonal antibody can be recycled to the cell culture vessel for complexing with additional t-PA.

TABLE 1 t-PA Expression in Confluent Cultures of CCD-18Co

| Sample | Avg. t-PA concn. (ng/ml) | Cell Density (cells/ml) | Avg. t-PA concn. ($\mu$g/$10^6$ cells) |
|---|---|---|---|
| 2 hours | 14 ± 2 | 1.1 × $10^5$ | 0.13 |
| 24 hours | 164 ± 0 | " | 1.5 |
| 48 hours | 152 ± 15 | " | 1.4 |
| 72 hours | 135 ± 6 | " | 1.2 |
| 96 hours | 126 ± 9 | " | 1.1 |

TABLE 2

Effect of anti-t-PA Mab on t-PA Expression in CCD-18Co

| Sample | Avg. t-PA concn. ng/ml | Cell Density (cells/ml) | Avg. t-PA concn. ($\mu$g/$10^6$ cells) |
|---|---|---|---|
| + Mab 79-7 1 $\mu$g/ml dose per day | | | |
| 24 hours | 163 ± 21 | 6 × $10^4$ | 2.7 |
| 48 hours | 298 ± 23 | 6.8 × $10^4$ | 4.4 |
| 72 hours | 405 ± 44 | 7.5 × $10^4$ | 5.4 |
| + Mab PAM-2 1 $\mu$g/ml per day | | | |
| 24 hours | 136 ± 9 | 6 × $10^4$ | 2.3 |
| 48 hours | 163 ± 15 | 6.6 × $10^4$ | 2.5 |
| 72 hours | 165 ± 22 | 7.7 × $10^4$ | 2.1 |
| CONTROL | | | |
| 24 hours | 121 ± 21 | 6.0 × $10^4$ | 2.0 |
| 48 hours | 156 ± 14 | 7.0 × $10^4$ | 2.3 |
| 72 hours | 138 ± 4 | 8.4 × $10^4$ | 1.6 |

TABLE 3

Recovery of t-PA from t-PA-Antibody Complex

| Sample | | ng/ml t-PA | Volume | Total ng t-PA | % of Total |
|---|---|---|---|---|---|
| PAM 2 COLUMN (#2) | Original fraction | 270 | 6.5 ml | 1755 | 100 |
| | UNADSORBED | 130 | 9.5 | 1240 | 70.4 |
| | Bound and Eluted | 73 | 4.8 | 350 | 20.0 |
| 79-7 COLUMN (#3) | Original fraction | 270 | 6.5 | 1755 | 100 |
| | UNADSORBED | *NP | 9.5 | — | — |
| | Bound and Eluted | 66.5 | 3.0 | 1995 | 112.4 |

*None detected

Various other examples will be apparent to the person skilled in the art after reading the present disclosure without departing from the spirit and scope of the invention, and it is intended that all such other examples be included within the scope of the appended claims.

What is claimed is:

1. The method of increasing the yield of tissue plasminogen activator in culture of mammalian cells comprising introducing antibodies to the t-PA of said cells into the cell culture nutrient medium, wherein said antibodies are such that they recognize an epitope on said t-PA and, when complexed with said t-PA, effectively prevent feedback inhibition of t-PA production by said cells, allowing the cells to grow, and then recovering t-PA from the t-PA-antibody complex thus formed in the conditioned medium by exchanging antibody in the complex for t-PA antibody immobilized on an inert support.

2. The method of claim 1 in which the cells are normal human colon fibroblast cells CCD-18Co (ATCC CRL-1459).

3. The method of claim 2 in which the t-PA antibodies are monoclonal antibody 79-7 (ATCC HB 1956).

4. The method of claim 1 in which the inert support is agarose.

5. The method of claim 1 in which the cells are normal human colon fibroblast cells CCD-18Co (ATCC CRL-1459), the t-PA antibodies are monoclonal antibody 79-7 (ATCC HB 1956), and the inert support is agarose.

6. The method of claim 1 in which the t-PA of the t-PA-antibody complex in the conditioned medium is bound to the t-PA antibody immobilized on the inert support at a NaCl concentration of up to about 0.15 molar and is eluted therefrom at a KSCN concentration of at least about 2 molar during the antibody exchange step for recovery of the t-PA.

7. The method of claim 6 in which the cells are normal human colon fibroblast cells CCD-18Co (ATCC CRL-1459), the t-PA antibodies are monoclonal antibody 79-7 (ATCC HB 1956), and the inert support is agarose.

* * * * *